United States Patent [19]

Rahn et al.

[11] Patent Number: 4,603,575

[45] Date of Patent: Aug. 5, 1986

[54] ELEMENTAL TRACER SYSTEM FOR DETERMINING THE SOURCE AREAS OF POLLUTION AEROSOL

[75] Inventors: Kenneth A. Rahn; Douglas H. Lowenthal, both of Narragansett, R.I.

[73] Assignee: Board of Governors for Higher Education, State of Rhode Island and Providence Plantations, Providence, R.I.

[21] Appl. No.: 686,655

[22] Filed: Dec. 27, 1984

[51] Int. Cl.⁴ .......................................... G01N 15/06
[52] U.S. Cl. ......................................... 73/28; 436/56
[58] Field of Search .......... 73/23, 28, 170 R, 432 PS; 436/56, 25, 26, 27, 28

[56] References Cited

U.S. PATENT DOCUMENTS 4,135,092  1/1979  Milly ....................................... 73/23
4,325,122  4/1982  Parks et al. ........................ 73/170 R
4,345,912  8/1982  Bartz ..................................... 436/26

Primary Examiner—Stephen A. Kreitman
Attorney, Agent, or Firm—Thompson, Birch, Gauthier & Samuels

[57] ABSTRACT

A method of determining source areas of pollution aerosol. Selected pollution derived, fine particle tracer elements from within the source region are measured. The measured results are expressed as ratios to one of the tracer elements. A signature of the source region is determined from modes in the logarithmic frequency of the ratios of the tracer elements. Measurements are made of the tracer elements from a receptor region and elemental ratios constructed. The elemental ratios from the receptor region are compared with the signatures from possible source regions to determine the most probable source region.

9 Claims, 7 Drawing Figures

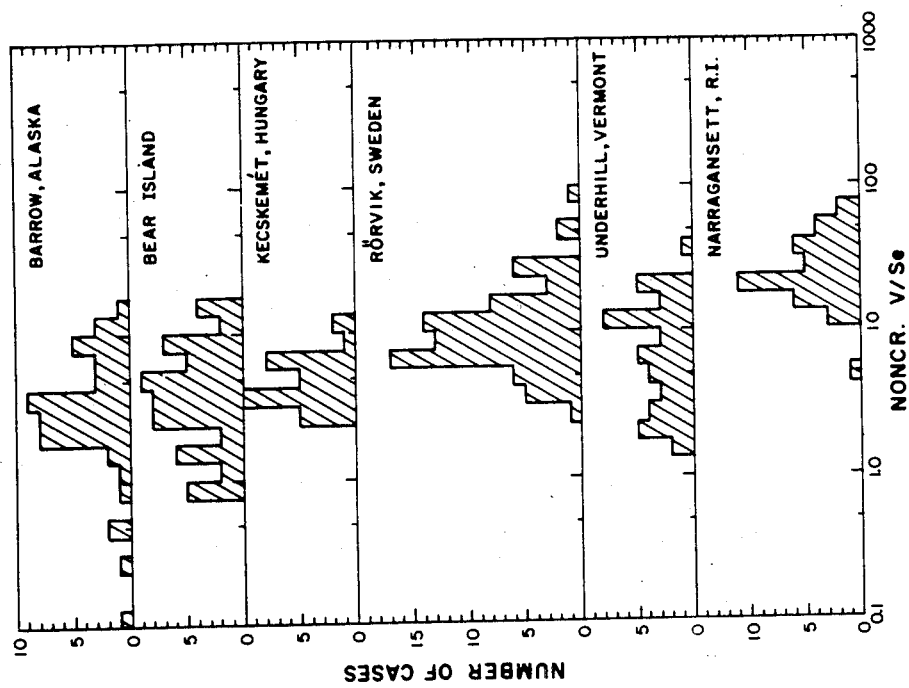
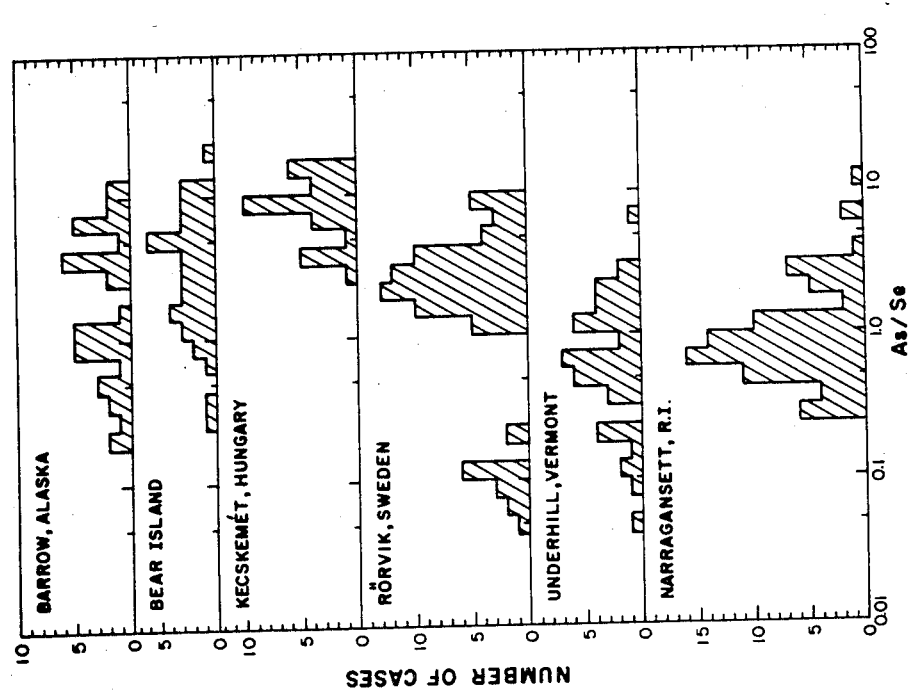
FIG. 1A
FIG. 1B

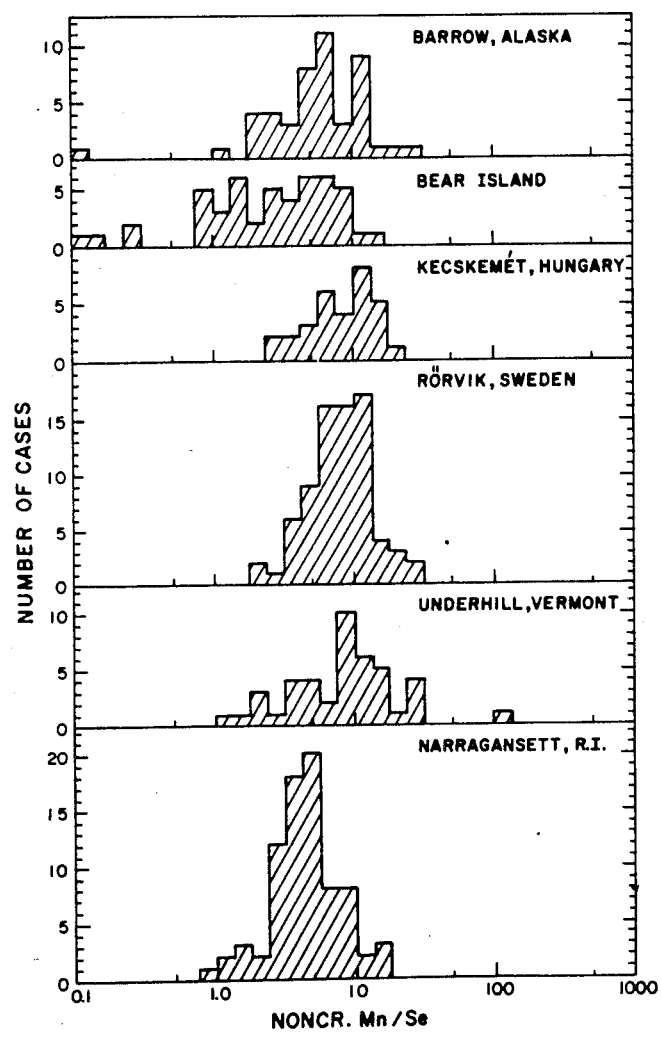
FIG. IE

ELEMENTAL TRACER SYSTEM FOR DETERMINING THE SOURCE AREAS OF POLLUTION AEROSOL

BACKGROUND AND BRIEF SUMMARY OF THE INVENTION

The routine transport of pollution aerosol through long distances is increasingly recognized as an important aspect of atmospheric science. Atmospheric transport on the scale of 1000 to 10,000 km is now invoked regularly to explain the results of aerosol studies in rural and remote areas. P. J. Samsonb, *J. Appl. Meteorol* 19, 1382 (1980); K. A. Rahn and R. J. McCaffrey, *Ann. N.Y. Acad. Sci.* 338, 486 (1980); R. D. Borys and K. A. Rahn, *Atoms. Environ.* 15, 1491 (1981); L. A. Barrie, R. M. Hoff, S. M. Daggupaty, ibid., p. 1407; C. Brosset, *Ambio* 5, 157 (1976).

But long-range transport has created a new set of interpretive problems. While it is relatively easy to identify pulses of transported pollution aerosols in remote areas which are otherwise clean, it is often difficult or impossible to pinpoint the source areas of these aerosols. (At distances of a few hundred kilometers or more, source areas are normally much more important than point sources).

Sheer distance can cause problems. For example, it has been extremely difficult to decide whether the important sources of pollution aerosol observed at Barrow, Alaska, are located in North America, Europe, or Asia. With air-mass trajectories from these sources being 5000 to 10,000 km or more in length and representing travel times of 5 to 10 days or more, pure meterological techniques have not led to consensus about even the continents of origin, much less particular regions within the continents. J. M. Miller, *Atoms. Environ.* 15, 1401 (1981); E. R. Reiter, ibid., p. 1465; D. E. Patterson and R. B. Husar, ibid., p. 1479.

The configuration of sources can also make identification difficult. In the northeastern United States, for example, where the source areas of acid aerosol and precipitation are currently in dispute, distances of transport are much shorter (1000 km or less) but the spatial pattern of sources is complex. As a result, trajectories to areas of concern such as the Adirondacks or New England often pass over several strong source areas in their last few hundred kilometers. No available transport model can reliably apportion the contributions of these sources to the final sulfate, acid, or other ubiquitous constituents of the pollution aerosol.

There is thus a need for a more direct way to identify distant sources of pollution aerosol. Such a capability would be of practical as well as scientific importance, because it could be extended ultimately to determining source areas of acid precipitation. It may cost as much as $20 billion to $100 billion to reduce emissions of sulfur dioxide in the eastern United States over the next decade; controlling the wrong sources would be a very costly error.

The present invention embodies a method to detect regional sources of pollution on a regional scale. The efforts to date in this field can only trace individual emitters over smaller distances.

Pollution aerosol contains all elements; no true tracers, or elements unique to specific source areas, exist. But it is reasonable to expect the proportions of at least some elements to vary with source area because different areas have different mixes of the major aerosol sources (combustion, industry, transportation, and so on), different mixes of fuels, fuels from different origins, different industrial bases, and different degrees of pollution control. However, the number of regional elemental signatures, the magnitude of their differences, and the elements involved cannot be predicted; they must be determined empirically.

In general, regional tracers as used in our invention are constructed and used quite differently from urban tracers. Elemental signatures used to deduce sources of urban aerosol by receptor-oriented techniques (G. E. Gordon, *Environ. Sci. Technol.* 14, 792 (1980).) are usually derived from either point sources or specific types of sources (automotive exhaust, for example). Regional aerosols, by contrast, are mixes of many sources and should thus resemble one another much more than signatures within an urban region should. Similarities among pollution aerosols have been recognized for years (K. A. Rahn, "*The chemical compositon of the atmospheric aerosol,*" Technical Report, Graduate School of Oceanography, University of Rhode Island (1976).), and many have doubted whether useful regional differences could be found. We have determined that characteristic regional signatures do exist, many of which are very different from one another.

The two keys to deriving regional signatures are finding the right elements and handling the data with the appropriate statistical techniques. The "marker-element" approach sometimes used in urban studies (where the contribution of a source is evaluated by a single element) cannot be used with regional signatures because of their great similarities. The opposite approach, constructing signatures from all available elements, is practiced in some urban studies but addes too much noise to regional pollution signatures. The best approach seems to be a compromise-limit regional signatures to those few elements with the greatest tracer power.

Several requirements should be met by elements and signatures before they can be used in a regional tracer system: the elements should be pollution-derived, sampled and measured accurately, emitted stably and homogeneously in each region, and present on particles small enough to be transported long distances; each signature should remain recognizable during transport. Our preliminary assessment indicates that all these requirements are met adequately; we illustrate several of them in the description that follows. Nevertheless, some of these requirements, such as conservation of proportions during transport, are sufficiently critical that we have built routine checks into our operating system.

In our invention a system in which the relative abundances of selected elements in pollution aerosol (suspended particles) are used to determine the region(s) from which it has originated. The technique can be applied at distances of hundreds to thousands of kilometers from the sources, i.e., in regions ranging from rural to very remote, and where conventional approaches such as emission inventories, air-mass trajectories, and long-range transport models fail. For example, both Canada and the United States now agree that the several long-range transport models currently in use for predicting the origins of sulfate and acidity are unverified and unverifiable in the near future. We thus view our elemental technique as a powerful alternative.

Our invention distinguishes from the known prior art in that we recognize and document the existence of regional elemental signatures. The technique described hereinafter represents our formalized method for developing these signatures and using them quantitatively.

The techniques has several key features. It preferably uses seven pollution-derived, fine-particle elements in the signatures (arsenic, selenium, antimony, zinc, indium, manganese, vanadium). These elements are chosen from the 40 or so that we can measure by neutronactivation analysis because they are the most pollution-derived and are determined best, i.e., have the lowest analytical uncertainties. This list of elements is not static; it can be altered as needed, and should expand in the future as other analytical techniques are employed. For elements such as manganese and vanadium, a substantial fraction of whose mass comes from suspended soil dust, only the pollution-derived component is used. It is important that only fine-particle elements be used in this tracer system, so that they will remain in the atmosphere for long periods and their proportions will not change during transport.

Regional signatures are preferrably built from the six elemental ratios to selenium rather than the seven absolute concentrations. Ratios are used to correct for changes in elemental concentration due to dispersion and removal during transport.

The regional signatures are built up from multiple samples at multiple sites within each region. Because any region can be influenced by aerosol from outside it, only some of the samples from a given region can be used to characterize it. They must be chosen from the total set of samples with care. We generally use some combination of a priori knowledge of the region, modal analysis of the frequency distributions of the elemental ratios, and meterological analysis to do this. To be safe, the signature of a region should not be considered known until samples inside and outside the region agree. From the final set of samples representing a region, geometric means and geometric standard deviations are calculated from each elemental ratio to selenium. The collection of six means and six standard deviations is the elemental signature of that region.

A sample of aerosol from a receptor region can be assigned to a most-likely source area by discriminant analysis, which compares the six elemental ratios to those of samples from possible source regions in a multivariate sense and assigns probabilities that the sample came from each region.

Contributions of several source regions to the signature elements can be determined by least-square apportionment, using various calculational routines and elemental weighting factors.

Contriubtions of several source regions to sulfate aerosol (formed mostly from $SO_2$ during transport) or other nonsignature constituents can be determined by regressing the regional coefficients of a suite of samples against their sulfate concentrations.

Unique features of our tracer technique are its set of seven elements and its regional approach. Elemental tracers have been used to determine the sources of urban aerosol for several years. Our regional approach, however, uses different elements, a different form for the signatures, builds up the signatures according to a different protocol, and manipulates them with different statistical techniques.

We have determined that well-defined regional signatures exist in both North America and Europe. In North America, we have measured both midwestern and coastal influences on pollution aerosol at Underhill, Vt.; Narragansett, R. I.; High Point, N. J.; and Allegheny Mountain, Pa. The meterology of many of the samples in question was sufficiently obscure that it could not have revealed their origins with any confidence. In Vermont, the majority of the sulfate aerosol in summer comes from the Midwest; in Rhode Island, it comes from the Northeast. We have also detected a signature from the nonferrous smelters of the Sudbury Basin and shown that their contributions to sulfate aerosol in New England during summer are small. The role of these smelters has been discussed for years; we have provided the first direct answers. In Europe, we have shown that the aerosol of a particularly strong pollution episode in Sweden and Finland came from East Europe, not West Europe or the United Kingdom. In the Arctic, we have shown that aerosol at both Barrow, Alaska and Bear Island (Norwegian Arctic) is dominated by Eurasian rather than North American sources. At each site, aerosols from different parts of Eurasia have been detected.

BRIEF DESCRIPTION OF THE DRAWINGS

FIGS. 1a, 1b, 1c, 1d, 1e and 1f show the frequency distributions of six elemental ratios at six sites in eastern North America, Europe, ad the Arctic.

DESCRIPTION OF THE PREFERRED EMBODIMENT

Figure 1F:
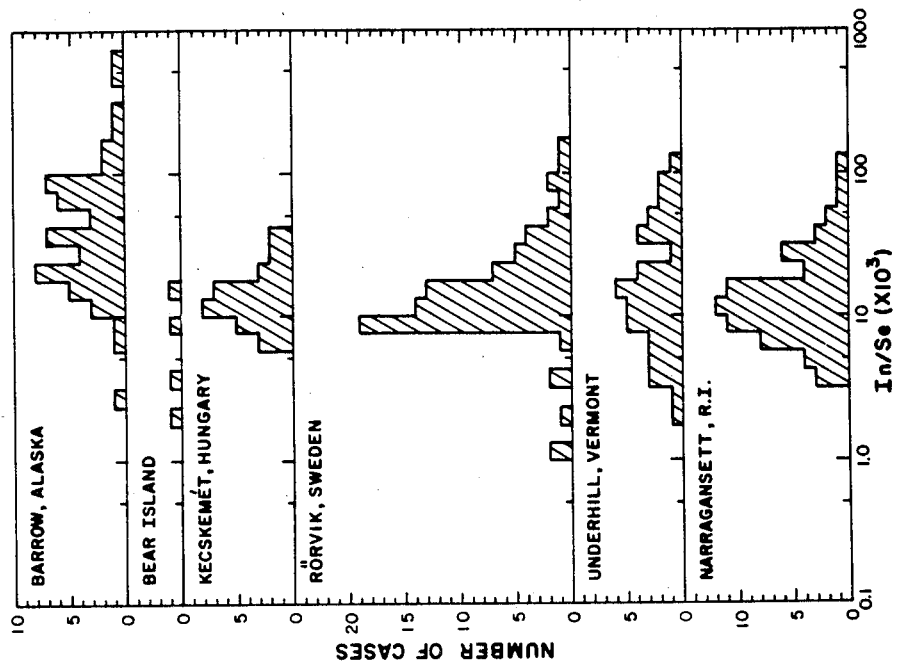

The first regional tracer was the noncrustal Mn/V ratio Atoms, Environ. 15, 1457 (1981). (The noncrustal component of an element is used here to mean the mass present in excess of that calculated from a crustal reference element like Al, Si, Fe or Ti, assumed to be totally crustal in the aerosol (a), and a crustal reference material such as bulk rock or soil (r). The formula typically used to calculate the noncrustal component of element X is Noncrustal $X_a$ = total $X_a$ − $Al_a(X/Al)_r$ In most cases, global mean crustal rock or soil is satisfactory; occasionally, local rock or soil must be used as reference material). This tracer was designed to determine whether Arctic aerosol originated mainly from Europe or eastern North America. The noncrustal Mn/V ratio demonstrated the general feasibility of regional elemental tracers and stimulated the development of more sophisticated tracing systems. At present, we are using a seven-element tracer system involving As, Sb, Se, Zn, In, noncrustal Mn, and noncrustal V. The design of this system and several of its applications are discussed below.

These seven elements were chosen from the 40 to 45 that we have measured by neutron activation as best meeting the criteria of being pollution-derived, fine-particle (The dividing line between fine and coarse aerosol is usually taken to be radius $\sim 1$ $\mu$m. This corresponds to the approximate breakpoint between (i) particules which penetrate to the lung and those which do not, (ii) coarser particles formed by mechanical subdivision (of soil and seawater, for example) and finer particles formed by coagulation or nucleation, and (iii) the original German "large" and "giant" ranges of particles.), and accurately analyzable (Instrumental neutron activation normally allows As, Sb, Se, Zn, and noncrustal V to be determined in replicate aerosol samples to uncertainties of 5 to 15 percent, and In and noncrustal Mn to 10 to 40 percent. Differences between elements in simultaneous samples are usually less than 10 percent; for ratios, most of this difference disappears.). Potential tracers rejected because of larger analytical uncertainties included Cu, Ni, Ga, Mo, Ag, Cd, Sn, W, Au, and Hg. With better analysis, any or all of these might be included in the system. Lead and elemental carbon are strong candidates which should also be investigated. Indium, whose analysis is poorer than those of the other six elements, was retained because of its great utility in tracing nonferrous smelters, K. A. Rahn, N. F. Lewis, D. H. Lowenthal, in *Receptor Models Applied to Contemporary Pollution Problems*, SP-48, Air Pollution Control Association, Pittsburgh, PA, 1982 p. 163.

Our regional signatures consist of six elemental ratios to Se. Ratios are used to normalize for variable meterological effects such as dispersion and removal; Se is used in the denominator because it is a general pollutant found at similar concentrations in diverse source areas and hence will not bias the ratios toward any particular region. In spite of Se's ubiquitous but modest vapor phase of 15 to 30 percent near the surface (B. W. Mosher and R. A. Duce, *J. Geophys. Res.* 88, 6761 (1983).) and its natural sources such as volcanoes, it works well as a normalizing element in regions as remote as the Arctic in winter. We tested Zn as an alternative denominator (because of its similarly low coefficient of variation) and obtained the same results as with Se. Other general pollution elements such as Pb or C might also be considered for the denominator.

The signature of a source region cannot be derived in a completely straightforward fashion because most regions can be affected by pollution aerosols transported from other regions. To eliminate such interference, we have developed a protocol which involves multiple samples at multiple sites inside and outside the region. At each site, at least 100 (ideally) daily samplers are taken and analyzed for the tracer elements. Logarithmic frequency distributions of the various X/Se ratios are then constructed and examined for the presence of modes, or maxima, which represent characteristic aerosols for the sites. The meterological characteristics such as of atmospheric stagnation can be combined with chemical characteristics of the samples in a mode to give a good idea of its source. By combining the modal information from several sites in a region, its aerosol may usually be distinguished from those transported from neighboring regions. Local aerosol may also be identified from periods of atmospheric stagnation. As a final check, regional signatures are verified by sampling downwind of the region. This also shows whether any elemental ratios change significantly during transport.

To date, we have used filter samples of total aerosol for our tracer system. In effect, this provides size-segregated data because the tracer elements chosen are mostely submicrometer. True fine-particle samples would probably improve the tracer system by reducing the variability of elemental ratios and allowing mixed-mode elements such as Fe, Co, and Cr to be considered. But how much the improvement would be is not yet known, and size-segregated samples are much smaller and not readily available from many regions of interest. When elemental tracer techniques are eventually applied to precipitation, total aerosol will be a more appropriate reference than fine-particle aerosol, for coarse particles are scavenged more efficiently by precipitation than are fine particles.

Factor analysis, while useful for understanding broad elemental relations and the general sources of pollution aerosol of a site, has not been particularly successful in selecting elements as tracers or defining regional signatures. The reason for this seems to be that any technique which is based solely on single measures of similarity between elements (such as correlations) in a collection of samples does not adequately reveal the complex relations implicit in mixed frequency distributions.

Figure 1C:
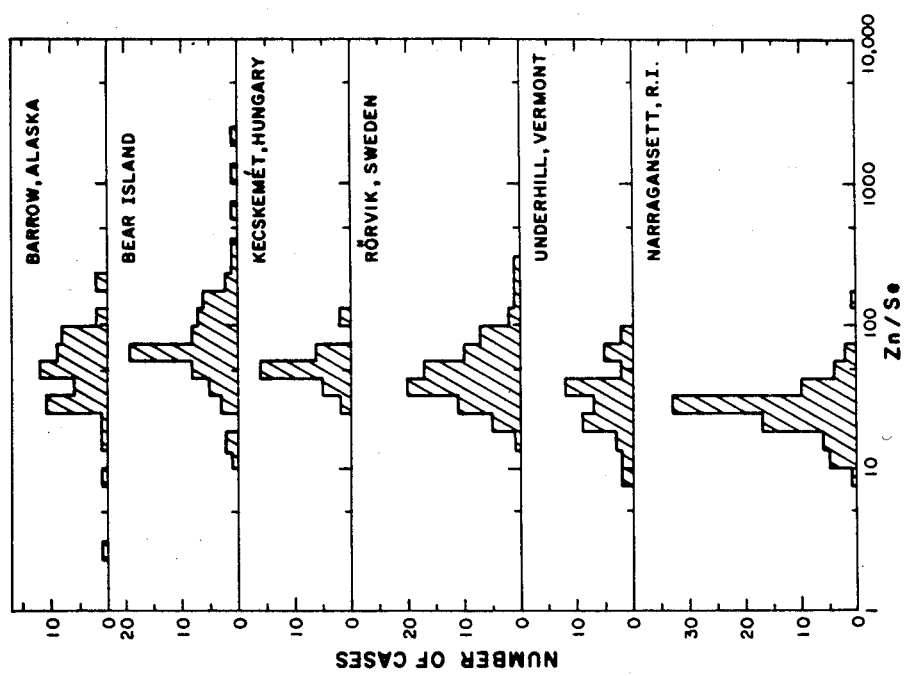
Figure 1D:
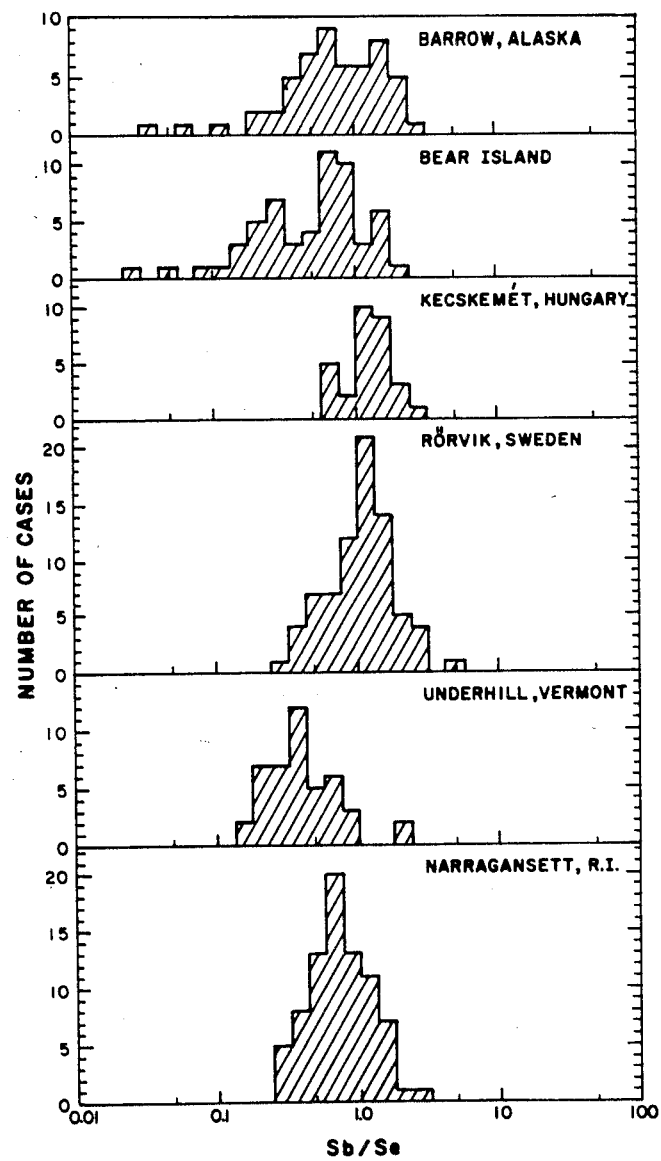

FIG. 1 shows the six X/Se distribution for six sites at which we have reasonable amounts of data: Narragansett, R. I., and Underhill, Vt., in eastern North America; Kecskemet, Hungary, and Rorvik, Sweden, in Europe; and Barrow, Alaska, and Bear Island, Norway, in the Arctic (Seventy-nine Narragansett samples taken semiweekly during February–April and June–August 1978 and January–March and June–September 1979; 43 Underhill samples taken daily during July–August 1982; 76 Rorvik samples taken for 1 to 3 days each during fall and winter 1981–1982; 31 Kecskemet samples taken daily during fall and winter 1981–1982; 66 Bear Island samples taken for 2 to 3 days each during winter 1977–1978; 54 Barrow samples taken simiweekly from October 1977 to May 1978). Depending on element and location, one or more modes are seen in each distribution. The modes are reasonably symmetric (that is, log-normal), with geometric standard deviations of 1.4 to 1.6 (68 percent of the points found within a total factor of 2 to 3). Some modes have geometric standard deviations as low as 1.2. The presence of these modes shows that a few major types of pollution aerosol are found at each site.

More types of pollution aerosol may be present at a site than are revealed directly by the major modes, however. Broader-than-normal modes may be composed of two or more unresolved modes, as seems often to be the case for Zn/Se and Sb/Se, for example. Small features may represent infrequent appearances of aerosols which are more important elsewhere. An example of this is the small upper mode of As/Se at Rorvik (ratios of 8 to 10), which coincides with the principal mode (6 to 12) at Kecskemet (we show below the upper mode at Rorvik was created by a pulse of aerosol from eastern Europe). Another example is the low shoulder of Zn/Se at Narragansett (ratios of 10 to 20), which has been resolved into a discrete mode by subsequent shorter period samples. The real number of modes in most distributions is not known and may be considerably larger than the number apparent from FIG. 1.

Membership in most modes is organized; that is, samples in a certain mode of one distribution are usually found together in other distributions. For example, the samples from eastern Europe which comprise the upper As/Se mode of Rorvik also comprise the low shoulder of noncrustal V/Se there (ratios of 3 to 6). This illustrates that well-defined pullution aerosols with recognizable signatures do exist. As shown below, they can usually be identified with specific geographic source areas.

At present, we use the modes of FIG. 1 only qualitatively. To derive signatures of pollution aerosol for specific regions, we use subsets of the modes composed of samples deemed most representative. With experience, it should be possible to increase the numbers of samples used to define signatures.

Twelve regional signatures, six from North America and six from Europe, are shown in Table 1. The signature of regional New England (NE) was derived from four daily samples at Underhill Aug. (4 to 7 1982), in aged Canada air masses which had not been affected by the large nonferrous smelters of the Sudbury Basin. The outstanding feature of this signature is its low As/Se ratio, which we interpret as indicating minimal coal influence. We have also detected this signature in Narragansett and South Portland, Me. (the small low-As mode at Narragansett in FIG. 1 is associated with this kind of aerosol.

gional, there). The Washington, D.C. (WASH), signature came from grand averages of individual average concentrations from ten sites in the Washington area during August and September 1976 (G. S. Kowalczyk, G. E. Gordon, S. W. Rheingrover, *Environ.Sci. Technol.* 16, 79 (1982). As in New York, Zn was reduced by 30 percent in an attempt to represent aerosol from the central mid-Atlantic states. The interior (INT) signature was derived from four daily samples in Underhill,

TABLE 1

Geometric mean elemental signatures for source aerosols in North America and Europe (geometric standard deviations in parentheses).

| Source | N | As/Se | Sb/Se | Noncrustal V/Se | Zn/Se | Noncrustal Mn/Se | In/Se (× 1000) |
|---|---|---|---|---|---|---|---|
| Individual sources | | | | | | | |
| SCANS | 5 | 2.8 (1.3) | 0.94 (2.0) | 24 (1.3) | 43 (1.5) | 5.2 (1.8) | 9.5 (1.7) |
| WEURS | 5 | 1.88 (1.2) | 1.01 (1.4) | 5.8 (1.3) | 37 (1.1) | 6.5 (1.2) | 13.1 (1.6) |
| WEURH | 5 | 3.5 (1.1) | 0.75 (1.3) | 7.2 (1.8) | 56 (1.4) | 6.8 (1.7) | 11.1 (2.2) |
| EEURF | 5 | 7.2 (1.2) | 1.33 (1.3) | 7.8 (1.2) | 54 (1.1) | 10.0 (1.2) | 13.1 (1.3) |
| EEURS | 3 | 7.3 (1.1) | 1.73 (1.1) | 4.8 (1.2) | 66 (1.1) | 13.7 (1.2) | 15.1 (1.2) |
| EEURH | 4 | 8.9 (1.0) | 1.18 (1.1) | 5.2 (1.3) | 48 (1.1) | 8.9 (1.8) | 9.8 (1.4) |
| NE | 4 | 0.13 (1.4) | 0.45 (1.3) | 11.3 (1.2) | 32 (1.2) | 9.2 (1.3) | 9.8 (1.9) |
| BOS | 3 | 0.68 (1.5) | 0.82 (1.8) | 35 (1.2) | 37 (1.1) | 4.1 (1.2) | 5.3 (1.1) |
| NYC | 3 | 1.10 (1.1) | 1.63 (1.7) | 11.1 (1.3) | 40 (1.1) | 6.5 (1.3) | 9.6 (1.6) |
| WASH | 4 | 1.46 (1.2) | 0.82 (1.2) | 9.9 (1.2) | 22 (1.2) | 4.0 (1.8) | 7.1 (1.2) |
| INT | 4 | 0.92 (1.2) | 0.28 (1.4) | 1.96 (1.4) | 10.8 (1.3) | 2.6 (1.5) | 3.9 (1.7) |
| SONT | 3 | 8.0 (1.2) | 0.75 (1.2) | 1.77 (1.9) | 57 (1.1) | 13.9 (1.1) | 46 (1.7) |
| Regional means | | | | | | | |
| SCANS | 5 | 2.8 (1.3) | 0.94 (2.0) | 24 (1.3) | 43 (1.5) | 5.2 (1.8) | 9.5 (1.7) |
| WEUR | 10 | 2.6 (1.4) | 0.87 (1.4) | 6.4 (1.6) | 45 (1.4) | 6.6 (1.5) | 12.1 (1.9) |
| EEUR | 12 | 7.8 (1.2) | 1.37 (1.2) | 6.0 (1.4) | 54 (1.1) | 10.4 (1.5) | 12.3 (1.3) |
| ECOAST | 14 | 0.58 (2.9) | 0.80 (1.8) | 13.8 (1.7) | 31 (1.3) | 5.7 (1.6) | 7.8 (1.6) |
| INT | 4 | 0.92 (1.2) | 0.28 (1.4) | 1.96 (1.4) | 10.8 (1.3) | 2.6 (1.5) | 3.9 (1.7) |
| SONT | 3 | 8.0 (1.2) | 0.75 (1.2) | 1.77 (1.9) | 57 (1.1) | 13.9 (1.1) | 46 (1.7) |
| Continental means | | | | | | | |
| EUR | 27 | 4.2 (1.8) | 1.08 (1.5) | 8.0 (1.9) | 49 (1.3) | 7.6 (1.6) | 11.6 (1.6) |
| NAMER | 21 | 0.93 (3.5) | 0.65 (1.9) | 7.1 (3.0) | 28 (1.8) | 5.6 (1.9) | 8.8 (2.4) |

The "Boston" (BOS) aerosol was derived from three daily samples at Narragansett when the winds came from the direction of Boston and Providence and $SO_2$ concentrations were high (July, 20 and Aug. 3 and 6 1982). The New York City (NYC) signature came from six semiweekly samples taken in midtown Manhattan during the 1977–1978 winter. In order to better apply this signature to summer samples elsewhere, we reduced its noncrustal V by 50 percent (K. A. Rahn, D. H. Lowenthal, and N. F. Lewis ["*Elemental tracers and source areas of pollution aerosol in Narragansett, Rhode Island.*" Technical Report, Graduate School of Oceanography, University of Rhode Island (1982)] show that noncrustal V in both New York City and Narragansett decreases from winter to summer by 50 percent relative to other pollution-derived elements.) To better simulate the regional signature near New York, we reduced the Zn, which is abnormally enriched in urban aerosol, by 30 percent (because roughly 30 percent of the Zn is from coarse particles and presumably local, not re- Vermont, in July 1982, when an unusually strong signal of coal was present and associated with winds from the south-southwest. This singature does not represent pure coal emissions but rather an area where coal emissions are unusually strong. The Canadian smelter (SONT) signal was derived from three samples in southern Ontario roughly 300 km east-southeast of Sudbury (K. A. Rahn, thesis, University of Michigan (1971). It is enriched in As and In. (The small groups of samples defining the signatures were representative distillations of larger sets of data; numbers of samples in each group were kept comparable for statistical purposes).

The samples from Kecskemet and Rorvik allowed us to construct six regional signatures for Europe, three from the East and three from the West. Signature EEURH came from four samples associated with the most prominent mode of As/Se in Kecskemet. Signature EEURS came from three samples at Rorvik during the most intense "black episode" (C. Brosset, Supra) of the past decade.

TABLE 2

Episode of east European aerosol at Sweden and Finland.

| Dates of Sample (1982) | Sulfate ($\mu$g m$^{-3}$) | As/Se | Sb/Se | Noncrustal V/Se | Zn/Se | Noncrustal Mn/Se | In/Se (× 10$^3$) |
|---|---|---|---|---|---|---|---|
| Rorvik, Sweden | | | | | | | |
| 11–13 January | 2.4 | 3.0 | 0.67 | 15.4 | 69 | 13.1 | 17.4 |
| 13–15 January | 5.4 | 9.6 | 2.4 | 50 | 52 | 26.5 | 31 |
| 15–18 January | 12.9 | 4.0 | 0.8 | 5.2 | 49 | 6.0 | <3 |
| 18–20 January* | 11.1 | 7.4 | 1.85 | 6.0 | 70 | 13.0 | 16.1 |
| 20–21 January* | 19.5 | 8.2 | 1.68 | 3.8 | 65 | 11.7 | 12.8 |
| 21–22 January* | 35.5 | 6.3 | 1.68 | 4.8 | 63 | 16.8 | 16.7 |
| 22–25 January | 8.3 | 3.3 | 1.83 | 4.2 | 33 | 4.5 | 7.6 |
| 25–27 January | 3.6 | 1.8 | 0.98 | 14.6 | 31 | 3.5 | 13.1 |

TABLE 2-continued
Episode of east European aerosol at Sweden and Finland.

| Dates of Sample (1982) | Sulfate ($\mu g\ m^{-3}$) | As/Se | Sb/Se | Non-crustal V/Se | Zn/Se | Non-crustal Mn/Se | In/Se ($\times 10^3$) |
|---|---|---|---|---|---|---|---|
| | | | Ahtari, Finland | | | | |
| 17–18 January | 6.5 | 3.4 | 0.60 | 9.4 | 54 | 3.8 | 7.2 |
| 18–19 January | 5.3 | 2.6 | 0.64 | 8.0 | 66 | 5.7 | 11 |
| 19–20 January* | 3.7 | 5.5 | 1.3 | 8.9 | 58 | 9.5 | 15 |
| 20–21 January* | 19.4 | 6.6 | 1.6 | 5.7 | 52 | 13 | 13 |
| 21–22 January* | 9.0 | 6.8 | 1.5 | 7.0 | 56 | 11 | 11 |
| 22–23 January* | 17.8 | 5.9 | 1.6 | 8.3 | 52 | 10 | 10 |
| 23–24 January | 0.95 | 4.6 | 0.86 | 10 | 52 | 7.6 | 18 |

*East European aerosol present.

As shown in Table 2, this aerosol was very different from that before and after the episode and had eastern European rather than western European characteristics. These samples made up most of the small upper mode of As/Se at Rorvik shown in FIG. 1. Signature EEURF came from four samples at Ahtari, southern Finland, during the same black episode. Table 2 also shows these samples and how they closely resembled aerosol at Rorvik during the same period. The two signatures of western Europe, WEURS and WEURH, were derived from five samples at Rorvik when the winds were from the southwest and fine samples at Kecskemet when the winds were from the west, respectively. For at least As/Se and noncrustal V/Se, these samples appeared in well-defined modes at the two sites. The last European signature is for Scandinavia (SCANS), as determined from periods of unusually high noncrustal V/Se at Rorvik, which usually coincided with weak circulation or winds from the north.

The western and eastern European signatures confirm the existence of general regional aerosols which appear at various sites in and around large source regions. Because the three eastern signatures are so similar, they can be combined into a general eastern European signature (EEUR), as shown in Table 1. Similarly, the two western European signatures can be combined into the general WEUR. As more data became available from eastern North America, it should be possible to construct general signatures there as well. For illustrative purposes, we have combined the four coastal signatures NE, BOS, NYC, and WASH into ECOAST, which is also shown in Table 1. (All samples from North America and Europe were combined to form the continental signatures NAMER and EUR.) Note that the principal modes of As/Se, noncrustal V/Se, and Zn/Se at Barrow and Bear Island agree quite well with the WEUR and EEUR modes at Rorvik and Kecskemet.

Some of the most significant features emerging from elemental tracers are that the tracing power varies widely from element to element, that most of the tracing power is vested in a very few elements, and that the discriminatory power of an element, as measured by the range of its X/Se ratio and its degree of modality, is similar at widely diverse sites. For example, As/Se and Zn/Se have, respectively, large ranges with well-defined multiple modes and small ranges with single modes at most sites. Thus some elements are inherently much better tracers than others. The reasons for this are probably geochemical. They may be related to large-scale elemental variations in the earth's crust.

TABLE 3
Two estimates of the relative discriminatory power of various elemental ratios on the 48 signature samples of Table 1.

| | Number of samples misclassified (out of 48) | | |
|---|---|---|---|
| Elemental ratio omitted | With 12 individual signatures | With 6 regional signatures | With 2 continental signatures |
| | 1 | 2 | 7 |
| As/Se | 6 | 13 | 13 |
| Sb/Se | 1 | 2 | 6 |
| Noncrustal V/Se | 3 | 6 | 7 |
| Zn/Se | 2 | 3 | 9 |
| Noncrustal Mn/Se | 1 | 4 | 7 |
| In/Se | 2 | 2 | 7 |
| As/Se, noncrustal V/Se | 13 | 19 | 10 |
| Noncrustal Mn/Se, In/Se* | 2 | | |
| Sb/Se, Zn/Se* | | 5 | |
| Sb/Se, Zn/Se, noncrustal Mn/Se, In/Se* | | | 8 |

*Ratios indicated by stepwise discriminant analysis to be lacking in discriminatory power.

Table 3 illustrates two ways to measure the relative discriminatory power of tracer elements. In the first, linear discriminant analysis (Linear discriminant analysis is used to define groups from observations with known attributes and then classify other observations into one of these grops (D. F. Morrisson, *Multivariate Statistical Methods* (McGraw Hill, New York, 1976). pp. 230–246). For linear discriminant analysis, we used a program in SAS-79 (SAS) Institute, Inc., Cary, NC 1979) on log-transformed data was used to classify the 48 signature samples of Table 1 into the 12, 6 and 2 groups shown in Table 3. Initially, all six of our X/Se ratios were used. Then the samples were reclassified with each of the ratios removed in turn. The greater the discriminatory power of a ratio, the more samples will be misclassified when it is removed. The results showed that As/Se and noncrustal V/Se had the greatest discriminatory power, Zn/Se had somewhat less power, and the other three ratios contributed little or nothing on the average. When both As/Se and noncrustal V/Se were removed, the extent of misclassification became greater than their summed individual effects. As a more sophisticated test of discriminatory power, stepwise discriminant analysis (In stepwise discriminant analysis, variables are added to the discriminant function in the order that they enhance the separation between groups. For stepwise discriminant analysis, we used a program in BMDP, *"Biomedical Computer Programs, P-Series"* (Univ. of California Press, Berkeley, 1979)) was applied to the six ratios (log-transformed) as they were used to segregate the 48 samples into groups of 12, 6, and 2 signatures. The results are shown at the bottom of Table 3. The only two ratios having good tracer power in all three cases were As/Se and noncrustal V/Se.

It may be possible to improve the discriminatory power of our ratios by using discriminant analysis in which elemental ratios are replaced by higher order terms as generated and selected by the group method of data handling (A. G. Ivakhnenko et al, in *Theoretical Systems Ecology*, E. Halfon, Ed. (Academic Press, New York, 1979), p. 325). The discriminatory power of optimized functions of ratios seems to be at least 20 to 40 percent greater than that of linear functions. Products involving As/Se and noncrustal V/Se are the most useful.

Empirical confirmation that certain elements are crucial to a successful regional tracer system was obtained by comparing our experience in southern Sweden with results of Lannefors et al. H. Lannefors, H. C. Hansson, L. Granat, *Atoms. Environ.* 17, 87 (1983) who took daily aerosol samples for 1 year at Sjoangen, 200 km northeast of Rorvik. Their data, which included S, Cl, K, Ca, Ti, V, Cr, Mn, Fe, Ni, Cu, Zn, Br, and Pb but lacked As, Se, Sb, and In, were unable to differentiate between aerosols from eastern and western Europe.

To test whether the criteria on which our seven-element tracer system was based—that the components be pollution-derived, fine-particle, and determined well by neutron activation—are unduly restrictive, we investigated the tracer power of nine other elements (Al, Sc, Cr, Co, Fe, La, Ce, Sm, Th) by means of stepwise discriminant analysis on the same 48 signature samples. These elements are as well determined as the seven basic tracers but are mostly coarse-particle in the aerosol (Cr, Co, and Fe usually have a fine-particle component and La and Ce occasionally do). In general, the tracer power of La, Ce and Sc was comparable to or better than that of Sb, In, and noncrustal Mn but less than that of As, noncrustal V, and Zn. The Al, Sm, and Th appeared to have little promise as tracers, and Fe, Co, and Cr behaved in an intermediate fashion. We do not know how the apparent tracer power of La, Ce and Se is partitioned between their coarse and fine-particle components. The fraction associated with coarse aerosol may be less useful than suggested by these signature samples, because coarse aerosol is not transported as efficiently as fine aerosol. Overall, it is probably prudent to measure as many elements as possible (both natural and pollution-derived) in the aerosol, with an eye toward occasions when they could be useful as tracers. Dust storms, volcanic eruptions, or bursts of aerosol from unexpected point sources of pollution may all provide transient aerosols with unusual signatures which could be understood by use of additional tracer elements.

Once discriminant analysis has been used to determine classification criteria from samples with distinctive signatures, one may classify nonsignature samples into those groups. In principle, the orginin of an aerosol sample could be determined from its chemical composition alone.

TABLE 4

Classification of nonsignature aerosol samples in North America and Europe.

| | Classification | | | | | |
|---|---|---|---|---|---|---|
| | With 12 Individual Signatures | | With 6 Regional Signatures | | With 2 Continental Signatures | |
| | North America | Europe | North America | Europe | North America | Europe |
| Narragansett, R.I. | 98 | 3 | 92 | 9 | 94 | 7 |
| Underhill, Vermont | 25 | 10 | 22 | 13 | 29 | 6 |
| Rorvik, Sweden | 21 | 45 | 19 | 47 | 28 | 38 |
| Kecskemet, Hungary | 0 | 22 | 0 | 22 | 0 | 22 |
| | | With five regional signatures | | | | |
| Bear Island. Norway (without In/Se) | | | 1 | 31 | | |
| Barrow, Alaska (without In/Se) | | | 5 | 28 | | |
| | SONT | NE | BOS | NYC | WASH | INT |
| Narragansett. R.I. | 0 | 17 | 17 | 8 | 37 | 22 |
| Underhill, Vermont | 1 | 14 | 1 | 7 | 3 | 9 |

Table 4 shows a geographic classification of unknown samples by our seven-element tracer system. In the upper part of the table, nonsignature samples from Narragansett, Underhill, Rorvik, and Kecskemet have been classified as North American or European based first on 12 individual signatures, then on six regional signatures, and finally on the two continental signatures of Table 1. In general, the posterior probability for membership in one of the source groups was greater than 90 percent. All samples from Kecskemet were classified correctly (as European). At Narragansett, 90 to 95 percent were classified correctly (as North American). At Underhill and Rorvik, however, only 60 to 80 percent were classified correctly. Similar results were obtained when the noncrustal Mn/Se and In/Se ratios were eliminated. Classifying samples by continent is a severe test, however, because it is much more difficult for entire continents than for regions to have distinct signatures.

The center of Table 4 shows how samples at Bear Island and Barrow were classified relative to the five more appropriate regional signatures (SCANS, WEUR, EEUR, ECOAST, INT). Only 1 of 32 (3 percent) and 5 of 33 (15 percent), respectively, were called North American. This confirms our earlier conclusions, reached independently, that Arctic pollution aerosol is strongly Eurasian in origin K. A. Rahn, ibid. 15, 1447 (1981); *Idojaras* 86, 1 (1982).

The bottom of Table 4 illustrates how the nonsignature samples at Narragansett and Underhill were classified relative to the six North American signatures. At Narragansett, the four coastal signatures accounted for three-quarters of the cases, with the other quarter coming from the interior signature. This result confirms with multielemental data the conclusions about dominance of coastal aerosol reached earlier from noncrustal Mn and V alone K. A. Rahn, D. H. Lowenthal, and N. F. Lewis ["*Elemental Tracers and source areas of pollution aerosol in Narrangansett, Rhode Island.*", Technical Report, Graduate School of Oceanography, University of Rhode Island (1982)]. At Underhill, on the other hand, the most common signature is New England (40 percent), followed by other East Coast (30 percent) and the interior (25 percent). Considering Underhill's location in northern New England, this distribution of sources is reasonable.

TABLE 5

Elemental concentrations in five source-area aerosols.

Concentration (ng m$^{-3}$)

| Element | NE | BOS | NYC | WASH | INT |
|---|---|---|---|---|---|
| As | 0.060 ± 0.033 | 0.49 ± 0.15 | 2.0 ± 0.2 | 3.2 ± 0.9 | 1.54 ± 0.40 |
| Sb | 0.143 ± 0.048 | 0.83 ± 0.41 | 3.1 ± 0.6 | 2.1 ± 0.7 | 0.55 ± 0.29 |
| Se | 0.37 ± 0.20 | 1.00 ± 0.60 | 1.88 ± 0.42 | 2.4 ± 0.7 | 1.78 ± 0.79 |
| Noncrustal V | 4.0 ± 1.7 | 35 ± 6 | 20 ± 4 | 23 ± 8 | 3.4 ± 1.0 |
| Zn | 11.1 ± 4.3 | 37 ± 3 | 70 ± 17 | 60 ± 12 | 18.2 ± 8.0 |
| Noncrustal Mn | 2.2 ± 0.3 | 4.2 ± 0.8 | 13.0 ± 1.1 | 9.2 ± 3.4 | 4.3 ± 2.4 |
| In | 0.0028 ± 0.0001 | 0.0050 ± 0.0040 | 0.0160 ± 0.0032 | 0.020 ± 0.006 | 0.0064 ± 0.0006 |

TABLE 6

Contributions of various source regions to elements in Narragansett aerosol sample GSO 176, 3 to 8 August 1979.

| | Weighting Factor | Concentration (ng m$^{-3}$) | | | | | |
|---|---|---|---|---|---|---|---|
| | | NE | BOS | WASH | INT | Total predicted | Observed |
| As | 300 | 0.03 | 0.06 | 0.20 | 0.36 | 0.65 | 0.67 |
| Sb | 30 | 0.08 | 0.10 | 0.13 | 0.13 | 0.44 | 0.55 |
| Se | 100 | 0.20 | 0.13 | 0.15 | 0.42 | 0.90 | 0.90 |
| Noncrustal V | 20 | 2.20 | 4.42 | 1.44 | 0.80 | 8.9 | 9.0 |
| Zn | 4 | 6.11 | 4.68 | 3.76 | 4.31 | 18.9 | 18.4 |
| Noncrustal | 0.4 | 1.21 | 0.53 | 0.58 | 1.02 | 3.34 | 2.00 |
| In | 100 | 0.0015 | 0.0006 | 0.00 | 0.0015 | 0.0036 | 0.0040 |

Discriminant analysis is used to determine which of several signatures is most likely to account for an aerosol sample. In actuality, however, most aerosol samples come from more than one source, either because of the history of the air mass or because of changes in it during sampling. By using least-squares techniques similar to those employed in previous chemical element balance analyses G. E. Gordon, *Environ. Sci. Technol.* 14, 792 (1980), a sample can be apportioned among the various regional aerosols which may have contributed to it (For least-squares apportionments of aerosol we used the program PETMIX, originally developed for petrologic studies [T. L. Wright and P. C. Doherty, *Geol. Soc. Am. Bull.* 81, 1995 (1970)], and a program in SAS-79). For the elemental concentrations of five regional aerosols listed in Table 5 (Tables 5 to 7 are from K. A. Rahn and D. H. Lowenthal, paper presented at the 17th Annual Conference on Trace Substances in Environmental Health, Columbia, Mo., June 13 to 16 1983, published May 1984.), Table 5 shows an apportionment for an August 1979 aerosol sample from Narragansett. In this sample, the abundances of six of the seven tracer elements were accounted for to better than 20 percent by four of the signatures (NYC gave a negative coefficient, so it was eliminated and the regression was rerun with four sources). The weighting factor in Table 6 is really two factors, one to scale the numerical values of the different elements and another, based on Table 3, to weight, As, Se, noncrustal V, and Zn relative to Sb, In, and noncrustal Mn. (The final apportionment is insensitive to weighting factor, however.) Note that about half of the As and Se were associated with the interior signal, whereas 60 to 80 percent of the Sb, Zn, In, and noncrustal Mn and more than 90 percent of the noncrustal V came from the coastal sources. This type of result is common for Narragansett during summer.

TABLE 7

Least-squares regional coefficients for 14 Narragansett aerosol samples from summer 1979

| | SO$^2$ | Regression Coefficient | | | | |
|---|---|---|---|---|---|---|
| Sample Dates | (μg m$^{-3}$) | NE | BOS | NYC | WASH | INT |
| 13-17 July | 8.63 | 0.66 | 0.11 | 0.11 | 0.02 | 0.07 |
| 17-24 July | 12.32 | 0.37 | 0.26 | 0.12 | 0.01 | 0.20 |
| 24-27 July | 11.24 | 0.00 | 0.36 | 0.00 | 0.00 | 0.56 |
| 27-31 July | 19.12 | 0.00 | 0.19 | 0.16 | 0.00 | 0.47 |
| 31 July–3 August | 16.49 | 0.76 | 0.00 | 0.04 | 0.00 | 0.34 |
| 3-8 August | 10.28 | 0.55 | 0.13 | 0.00 | 0.06 | 0.24 |
| 8-10 August | 5.47 | 0.56 | 0.08 | 0.22 | 0.00 | 0.23 |
| 10-14 August | 10.49 | 0.30 | 0.37 | 0.00 | 0.00 | 0.19 |
| 14-17 August | 8.31 | 1.17 | 0.07 | 0.19 | 0.00 | 0.00 |
| 17-21 August | 12.14 | 0.47 | 0.35 | 0.00 | 0.02 | 0.00 |
| 21-24 August | 22.48 | 0.38 | 0.47 | 0.09 | 0.00 | 0.00 |
| 24-28 August | 12.90 | 0.78 | 0.17 | 0.00 | 0.00 | 0.16 |
| 28-31 August | 11.00 | 0.80 | 0.05 | 0.02 | 0.00 | 0.14 |
| 31 August–4 September | 8.71 | 0.55 | 0.16 | 0.00 | 0.00 | 0.27 |

Table 7 summarizes the apportionments of 14 consecutive semiweekly samples from Narragansett during summer 1979, and shows that the mix of sources can vary strongly in response to large-scale meterology. During summer 1979, Narragansett had two major sulfate episodes, one in July and one in August. The first was a "typical" summer episode, with winds from the south to west. The second episode was different, however. It had the highest summer sulfate seen to that time in Narragansett but the lowest (most northeastern) noncrustal Mn/V ratios and the lowest As. Meterological maps showed that this episode was the result of large-scale stagnation in the Northeast of air which had originated largely in the upper Great Lakes and Canada. Thus, the first episode appeared to be mid-Atlantic or interior in origin, whereas the second appeared to be more than from New England and Canada.

The apportionments bore out these observations. The first episode had high regression coefficients from the interior, normal coefficients from Boston, and low coefficients from New England. The second episode, by contrast, had zero coefficients from the interior and normal to high coefficients from Boston and New England. Washington aerosol was negligible throughout the period; contributions from the New York area were low to moderate and irregular.

Although our tracer system is based on primary pollution elements, that is, those emitted directly as aerosol, an important use of the system will be to understand the regional origins of secondary species, such as sulfate and acidity, which are formed in the atmosphere from primary precursors. Sulfate is the most abundant constituent of many remote aerosols, and both sulfate and acidity are of great concern in acid deposition.

Strictly speaking, primary constituents cannot trace secondary constituents. Near strong sources of (primary) aerosol, such as large urban or industrial areas, our tracer system should work poorly for sulfate. Outside such areas, where regional aerosols dominate, a primary tracer system should work better, although there may still be difficulties. In remote areas, primary tracers should work still better because most of the primary precursors, such as $SO_2$, will have been converted or otherwise removed; that is, the secondary species will have reached quasi-stable proportions. Under these conditions, the aged regional aerosols would effectively contain a sulfate component linked to the primary signature elements.

Figure 2:
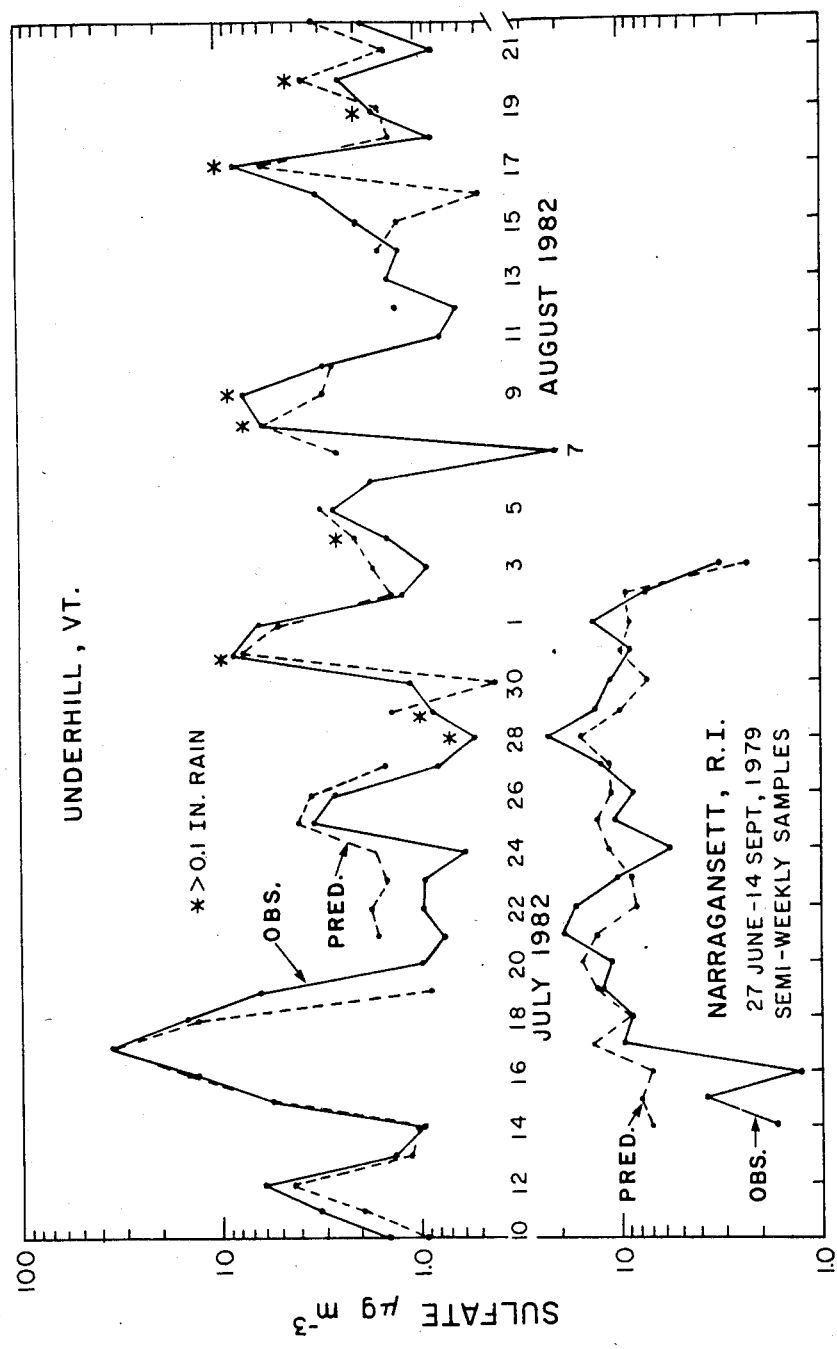
FIG. 2 shows the observed and predicted sulfate for 21 semiweekly samples during June tp September 1979.

This appears to be the situation at Underhill, Vt., for example. In a series of 39 daily samples from July and August 1982, we determined the "effective" sulfate in the various regional signatures by first apportioning the seven tracer elements, then regressing the sulfate of each sample against the regional coefficients derived from that sample. The results gave the following approximate concentrations of sulfate: $21\pm1$ g m$^{-3}$ for the interior signature (INT), $7\pm3$ μg m$^{-3}$ for the mid-Atlantic region (WASH), and $3\pm1$ μg m$^{-3}$ for the local aerosol (NE). Based on these values, the predicted sulfate concentrations generally reproduced the observed values to within 25 percent (FIG. 2). This accuracy is comparable to that obtained for the primary tracer elements. In particular, each of the peaks and valleys of sulfate was predicted.

At Narragansett, Rhode Island, however, the same approach gave poorer results. FIG. 2 shows the observed and predicted sulfate for 21 semiweekly samples during June to September 1979. The fractional errors were twice as large as at Underhill, neither peaks or valleys were predicted correctly, and a period of low sulfate at the beginning was missed entirely. This behavior is consistent with Narragansett's less remote location and with the abundant $SO_2$ observed there even during summer (2 to 20 g m$^{-3}$) (T. R. Fogg, personal communication). The "noise" in sulfate at Narragansett most likely results from variable and unpredictable oxidation of this subregional $SO_2$, on a scale too small to be seen at Underhill. Time traces of the elements at Narragansett are considerably more irregular relative to each other and to sulfate than at Underhill. Thus, it appears that both primary and secondary aerosol of the coastal Northeast are more local in origin than those in interior New England and that control of this aerosol and its deposition will require different strategies for different parts of the Northeast.

We claim:

1. A method to determine regional sources of pollution aerosol which includes:
    (a) selecting empirically a small number of suitable tracer elements which are pollution-derived, associated with submicron-sized particles, and accurately analyzable in the aerosol;
    (b) measuring the concentrations of each tracer element in multiple samples of regionally-representative aerosol at multiple sites in each source region whose signature is to be determined;
    (c) expressing the measured results as ratios to one of the tracer elements;
    (d) defining the elemental signature of the source region as the collection of elemental ratios and associated standard deviations which best represents that region's aerosol;
    (e) determining the source region's signature from modes in the logarithmic frequency distributions of the elemental ratios of samples taken in source region;
    (f) measuring the concentrations of each tracer element in multiple samples of an aerosol from a receptor region;
    (g) comparing the elemental ratios from the receptor region to the signatures from possible source regions to determine the most probable source region.

2. The method of claim 1 wherein the tracer elements are selected from the group consisting essentially of As, Sb, Se, Zn, In, noncrustal Mn, noncrustal V, Pb, Cd, Ag, C, and combinations thereof.

3. The method of claim 1 wherein the common denominator of the elemental ratios is selected from the group consisting essentially of Se, Zn, Pb, and C.

4. The method of claim 1 which includes:
    checking the stability during transport of a regional signature determined solely within a region by measurements outside the region.

5. The method of claim 1 which includes:
    identifying the perturbing effects of a local source by performing factor analysis on the raw data from a given site;
    isolating the local source on its own factor;
    determining the composition of the source from that factor; and
    eliminating the perturbing effects of that source by considering it as a separate signature subsequently.

6. The method of claim 1 which includes:
    determining the most probable area of origin of unknown samples by discriminant analysis of elemental ratios.

7. The method of claim 1 which includes:
    apportioning aerosol samples of mixed origin into regional contributions by least-squares fitting of the signatures (element by element) to the sample.

8. The method of claim 1 which includes:
    apportioning secondary constituents such as sulfate or other primary constituents such as elemental carbon, in a series of ratios at a single site, into regional contributions by regressing their concentrations against the regional coefficients of the samples.

9. A method to determine regional sources of pollution aerosol which includes:

(a) selecting empirically a small number of suitable tracer elements which are pollution-derived, associated with submicron-sized particles, and accurately analyzable in the aerosol;

(b) measuring the concentrations of each tracer element in multiple samples of regionally-representative aerosol at multiple sites in each source region whose signature is to be determined;

(c) expressing the measured results as ratios to one of the tracer elements;

(d) defining the elemental signature of the source region as the collection of elemental ratios and associated standard deviations which best represents that region's aerosol;

(e) determining the source region's signature from the characteristics of samples taken during periods of atmospheric stagnation;

(f) measuring the concentrations of each tracer element in multiple samples of an aerosol from a receptor region;

(g) comparing the elemental ratios from the receptor region to the signatures from possible source regions to determine the most probable source region.

* * * * *